United States Patent

Takeshiba et al.

Patent Number: 4,603,201
Date of Patent: Jul. 29, 1986

[54] PROCESS FOR PRODUCING ANTIFUNGAL OYRIDAZINONE DERIVATIVES

[75] Inventors: Hideo Takeshiba; Takao Kinoto; Teruomi Jojima, all of Hiromachi, Japan

[73] Assignee: Sankyo Company Limited, Tokyo, Japan

[21] Appl. No.: 724,800

[22] Filed: Apr. 19, 1985

Related U.S. Application Data

[63] Continuation of Ser. No. 472,671, Mar. 7, 1983, abandoned.

[30] Foreign Application Priority Data

Mar. 19, 1982 [JP] Japan ................... 57-44193

[51] Int. Cl.$^4$ .............. C07D 237/06; A61K 31/50
[52] U.S. Cl. ................................ 544/238
[58] Field of Search ............ 544/238, 239; 514/247

[56] References Cited

U.S. PATENT DOCUMENTS 4,052,395 10/1977 Jojima et al. .............. 424/250
4,255,571 3/1981 Müller .......................... 544/239

FOREIGN PATENT DOCUMENTS 2435244 2/1976 Fed. Rep. of Germany.
56-428 11/1981 Japan.

Primary Examiner—Nicholas S. Rizzo
Attorney, Agent, or Firm—Frishauf, Holtz, Goodman & Woodward

[57] ABSTRACT

Compounds of formula (I):

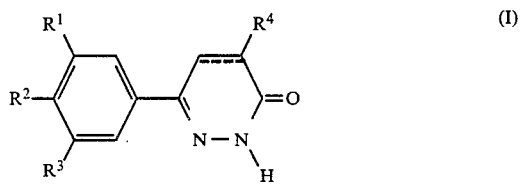

[wherein $R^1$ and $R^3$ represent hydrogen or halogen atoms, $R^2$ represents a hydrogen or halogen atom or a lower alkyl or alkoxy group (provided $R^1$, $R^2$ and $R^3$ are not simultaneously hydrogen), ═══ represents a single or double carbon-carbon bond and, where it is a single bond, $R^4$ represents a group of formula —$SR^5$ (wherein $R^5$ represents an optionally substituted alkyl, phenyl, aralkyl or pyridyl group or a lower alkenyl group) and, where it is a double bond, $R^4$ represents hydrogen] can be prepared by reacting a compound of formula (II):

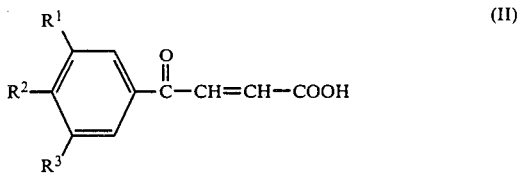

with a compound of formula $R^6H$ [where $R^6$ represents a group —$SR^5$, a group —$SR^7$ (where $R^7$ represents a group of formula

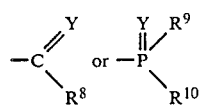

and Y represents oxygen or sulphur, $R^8$ and $R^9$ represent lower alkoxy groups and $R^{10}$ represents a lower alkoxy, lower alkyl or phenyl group), a methoxy group or a halogen atom] to give a compound of formula (IV):

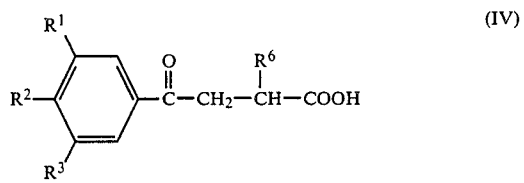

or, where $R^6$ represents a methoxy group, a methyl ester thereof; reacting this compound with hydrazine to give a compound of formula (V):

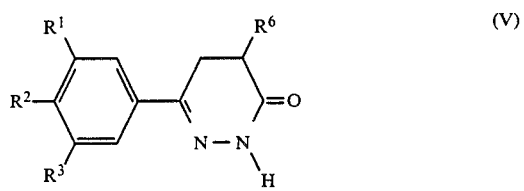

or (VI):

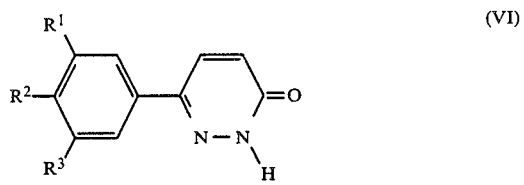

and, if necessary, treating the compound of formula (V) with an acid or a base to produce the compound of formula (VI). All of the compounds of formula (I) are valuable antifungal agents and compounds of formula (V) where $R^6$ represents a group of formula —$SR^5$ are novel compounds.

35 Claims, No Drawings

PROCESS FOR PRODUCING ANTIFUNGAL OYRIDAZINONE DERIVATIVES

This application is a continuation of application Ser. No. 472,671, filed Mar. 7, 1983, now abandoned.

BACKGROUND TO THE INVENTION

The present invention relates to a process for producing both known 6-(substituted phenyl)-3(2H)pyridazinones, which are known to have valuable antifungal activity, and certain novel, closely related, compounds.

United Kingdom patent specification No. 1,533,010 (which corresponds to U.S. Pat. No. 4,052,395) discloses a series of 6-(substituted phenyl)-3(2H)pyridazinone compounds, which are said to have valuable fungicidal activity. Of the compounds disclosed in this specification, 6-(3,5-dichloro-4-methylphenyl)-3(2H)pyridazinone has been found to have particularly good activity, rendering it suitable for commercialisation; specifically, it has a broad antimicrobial spectrum and is very useful as an agricultural fungicide, particularly for the prevention of sheath blight.

The process disclosed in the aforementioned United Kingdom patent specification for the preparation of this compound comprises reacting 4-(3,5-dichloro-4-methylphenyl)-4-oxobutyric acid with hydrazine to prepare 6-(3,5-dichloro-4-methylphenyl)-4,5-dihydro-3(2H)pyridazinone, which is then dehydrogenated. This process is, however, not wholly satisfactory, in that the preparation of the starting material, 4-(3,5-dichloro-4-methylphenyl)-4-oxobutyric acid, is difficult, the process is expensive and control of the reaction is a problem as the dehydrogenation step is an exothermic reaction.

An alternative process for preparing this compound using the method disclosed in Japanese patent publication No. 428/81 comprises reacting 4-(3,5-dichloro-4-methylphenyl)-4-oxo-2-butenoic acid with methanol at 20°–50° C., in the presence of anhydrous potassium carbonate, to give potassium 4-(3,5-dichloro-4-methylphenyl)-2-methoxybutyrate, converting this compound to the corresponding free acid and then reacting the acid with hydrazine. This reference does not exemplify its process using 4-(3,5-dichloro-4-methylphenyl)-4-oxo-2-butenoic acid to produce the pyridazinone identified herein. The process of the reference, however, has the disadvantage that side reactions often occur producing various by-products, with the result that the purity of the product is low and, because of the nature of the impurities, purification is difficult.

BRIEF SUMMARY OF INVENTION

We have now discovered a method of preparing 6-(3,5-dichloro-4-methylphenyl)-3(2H)pyridazinone and certain related compounds, which method enables many of the disadvantages of the prior art to be overcome. Indeed, in certain instances, it is possible to obtain the desired compounds in yields approaching 100% and with such a degree of purity that, once the compound has been separated from the reaction mixture, no specific purification step is required. Moreover, in the course of one aspect of the method of the invention, a series of novel compounds having excellent antifungal activity has also been discovered.

Accordingly, the present invention provides a process for preparing a compound of formula (I):

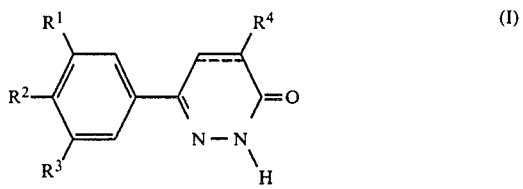

[in which:

$R^1$ and $R^3$ are the same or different and each represents a hydrogen atom or a halogen atom;

$R^2$ represents a hydrogen atom, a lower (i.e. $C_1$–$C_6$) alkyl group, a lower (i.e. $C_1$–$C_6$) alkoxy group or a halogen atom, provided that at least one of $R^1$, $R^2$ and $R^3$ represents a group or atom other than hydrogen;

‾‾‾‾‾‾ represents a single or double carbon-carbon bond; and where ‾‾‾‾‾‾ represents a single bond, $R^4$ represents a group of formula —$SR^5$ (in which $R^5$ represents an optionally substituted alkyl group, a lower (i.e. $C_2$–$C_6$) alkenyl group, an optionally substituted phenyl group, an optionally substituted aralkyl group or an optionally substituted pyridyl group) and, where ‾‾‾‾‾‾ represents a double bond, $R^4$ represents a hydrogen atom]

which process comprises:

(a) reacting a compound of formula (II):

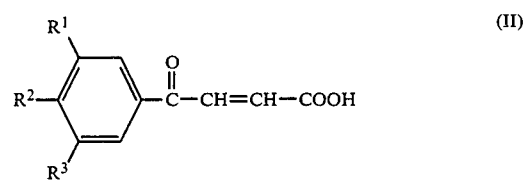

(in which $R^1$, $R^2$ and $R^3$ are as defined above) with a compound of formula (III):

$R^6H$     (III)

[where $R^6$ represents a group of formula —$SR^5$ ($R^5$ being as defined above), a group of formula —$SR^7$ (where $R^7$ represents a group of formula

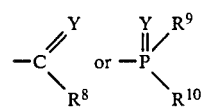

and Y represents an oxygen atom or a sulphur atom, $R^8$ and $R^9$ each represent lower alkoxy groups and $R^{10}$ represents a lower alkoxy group, a lower alkyl group or a phenyl group), a methoxy group or a halogen atom], provided that, where $R^6$ represents a methoxy group, the reaction is effected in the presence of a hydrogen halide, to give a compound of formula (IV):

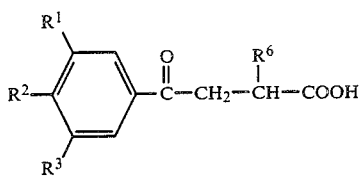

(IV)

(where $R^1$, $R^2$, $R^3$ and $R^6$ are as defined above) or, where $R^6$ represents a methoxy group, a methyl ester thereof;

(b) reacting the product of step (a) with hydrazine, optionally in the presence of hydrogen or hydroxy ions, to give a compound of formula (V):

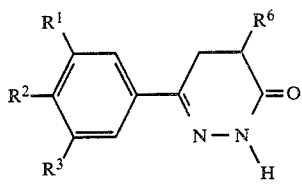

(V)

(in which $R^1$, $R^2$, $R^3$ and $R^6$ are as defined above) or a compound of formula (VI):

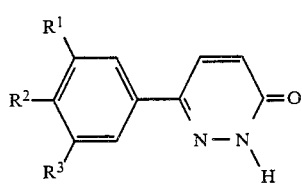

(VI)

(in which $R^1$, $R^2$ and $R^3$ are as defined above); and (c) optionally treating said compound of formula (V) with an acid or a base to produce said compound of formula (VI).

Of the compounds produced by the process of the invention, those compounds of formula (VII):

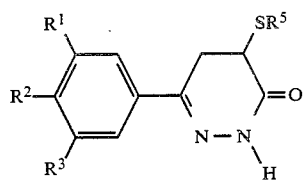

(VII)

(in which $R^1$, $R^2$, $R^3$ and $R^5$ are as defined above), that is to say compounds of formula (I) in which represents a carbon-carbon single bond and $R^4$ represents a group of formula $-SR^5$, are novel and have valuable antifungal activity.

The remaining compounds of formula (I), i.e. compounds of formula (VI) as defined above, are known, inter alia from United Kingdom patent specification No. 1,533,010 and also have valuable antifungal activity.

DETAILED DESCRIPTION OF INVENTION

In the compounds of the invention, where $R^1$, $R^2$ or $R^3$ represents a halogen atom, this may be a chlorine, bromine, fluorine or iodine atom, more preferably a chlorine or bromine atom.

Where the group represented by $R^2$ is a lower alkyl group, this is preferably a $C_1$-$C_4$ alkyl group, for example a methyl, ethyl, propyl, isopropyl or butyl group, more preferably a methyl group. Where the group represented by $R^2$ is a lower alkoxy group, this is preferably a $C_1$-$C_4$ alkoxy group, for example a methoxy, ethoxy, propoxy or butoxy group, more preferably a methoxy group.

In the compounds of formula (I) where $R^4$ represents a group of formula $-SR^5$ and in the compounds of formula (VII), where $R^5$ represents an alkyl group, this may be a substituted or unsubstituted alkyl group. In the case of the unsubstituted alkyl groups, these are preferably $C_1$-$C_6$ alkyl groups (such as the methyl, ethyl, propyl, isopropyl, butyl, t-butyl, pentyl or hexyl groups. In the case of the substituted alkyl groups, the substituents are preferably hydroxy, lower (preferably $C_1$-$C_4$) alkoxy, carboxy or alkoxycarbony (preferably $C_2$-$C_5$ alkoxycarbonyl) groups and the alkyl groups themselves are preferably $C_1$-$C_4$ groups; although two or more substituents may be present, in which case the substituents may be the same or different, we prefer that each alkyl group should bear only one substituent. Examples of such substituted alkyl groups which may be represented by $R^5$ include the 2-hydroxyethyl, 3-hydroxypropyl, 2-methoxyethyl, carboxymethyl, 1-carboxyethyl, 2-carboxyethyl, 3-carboxypropyl, 2-carboxypropyl, ethoxycarbonylmethyl, 2-methoxycarbonylethyl and 2-ethoxycarbonylethyl groups.

Where $R^5$ represents an alkenyl group, this is preferably a $C_3$ or $C_4$ alkenyl group, for example a 2-propenyl, 2-butenyl or 2-methyl-2-propenyl group. Where $R^5$ represents a phenyl, aralkyl or pyridyl group, these groups may be substituted or unsubstituted. In the case of the substituted phenyl, aralky or pyridyl groups, the substituents are preferably selected from halogen atoms (e.g. chlorine, bromine, fluorine or iodine), lower (preferably $C_1$-$C_4$) alkyl groups (e.g. methyl, ethyl, propyl or butyl groups) or nitro groups. Examples of such groups which may be represented by $R^5$ include the phenyl, 4-methylphenyl, 4-chlorophenyl, 4-nitrophenyl, benzyl, phenethyl, 4-methylbenzyl, 4-chlorobenzyl, 4-nitrobenzyl, 2-pyridyl, 3-pyridyl, 4-pyridyl, 3-nitro-2-pyridyl, 4-chloro-2-pyridyl and 6-methyl-3-pyridyl groups.

The preferred compounds of the invention are those in which:

either $R^1$ represents a halogen atom and $R^2$ and $R^3$ both represent hydrogen atoms;

or $R^1$ and $R^3$ both represent halogen atoms and $R^2$ represents a lower alkyl or lower alkoxy group;

and, where $R^4$ represents a group of formula $-SR^5$, $R^5$ represents an alkyl group (especially a methyl group), a 2-hydroxyethyl group, a carboxymethyl group, a carboxyethyl group, a (lower alkoxy)carbonylmethyl group or a (lower alkoxy)carbonylethyl group.

The most preferred compounds of the invention are those in which:

either $R^1$ and $R^3$ both represent chlorine atoms and $R^2$ represents a methyl group and, where $R^4$ represents a group of formula $-SR^5$, $R^5$ represents a methyl, carboxymethyl, carboxyethyl, (lower alkoxy)carbonylmethyl or (lower alkoxy)-carbonylethyl group;

or $R^1$ represents a bromine atom and $R^2$ and $R^3$ both represent hydrogen atoms, and, where $R^4$ represents a group of formula $-SR^5$, $R^5$ represents a methyl or 2-hydroxyethyl group.

The most preferred compound of formula (VI) is that in which $R^1$ and $R^3$ both represent chlorine atoms and $R^2$ represents a methyl group, that is to say the compound 6-(3,5-dichloro-4-methylphenyl)-3(2H)pyridazinone, already referred to.

Examples of the novel compounds of formula (VII) are given in the following list; the compounds are hereinafter, where appropriate, referred to by the numbers appended to them in this list.

1. 6-(3-Bromophenyl)-4-methylthio-4,5-dihydro-3(2H)-pyridazinone.
2. 6-(3-Bromophenyl)-4-ethylthio-4,5-dihydro-3(2H)-pyridazinone.
3. 6-(3-Bromophenyl)-4-isopropylthio-4,5-dihydro-3(2H)-pyridazinone.
4. 6-(3-Bromophenyl)-4-(2-hydroxyethyl)thio-4,5-dihydro-3(2H)pyridazinone.
5. 6-(3-Bromophenyl)-4-(2-carboxyethyl)thio-4,5-dihydro-3(2H)pyridazinone.
6. 6-(3-Bromophenyl)-4-phenylthio-4,5-dihydro-3(2H)-pyridazinone.
7. 6-(3-Bromophenyl)-4-(3-nitro-2-pyridyl)thio-4,5-dihydro-3(2H)pyridazinone.
8. 6-(4-Methylphenyl)-4-methylthio-4,5-dihydro-3(2H)-pyridazinone.
9. 6-(4-Methoxyphenyl)-4-methylthio-4,5-dihydro-3(2H)-pyridazinone.
10. 6-(3,4-Dichlorophenyl)-4-methylthio-4,5-dihydro-3(2H)pyridazinone.
11. 6-(3,4-Dichlorophenyl)-4-ethylthio-4,5-dihydro-3(2H)pyridazinone.
12. 6-(3,4-Dichlorophenyl)-4-isopropylthio-4,5-dihydro-3(2H)pyridazinone.
13. 6-(3,4-Dichlorophenyl)-4-(2-hydroxyethyl)thio-4,5-dihydro-3(2H)pyridazinone.
14. 4-(2-Carboxyethyl)thio-6-(3,4-dichlorophenyl)-4,5-dihydro-3(2H)pyridazinone.
15. 6-(3,5-Dichlorophenyl)-4-(2-methoxyethyl)thio-4,5-dihydro-3(2H)pyridazinone.
16. 6-(3-Bromo-4-chlorophenyl)-4-methylthio-4,5-dihydro-3(2H)pyridazinone.
17. 6-(3-Bromo-4-chlorophenyl)-4-(1-carboxyethyl)thio-4,5-dihydro-3(2H)pyridazinone.
18. 6-(3-Bromo-4-fluorophenyl)-4-(4-chlorophenyl)thio-4,5-dihydro-3(2H)pyridazinone.
19. 6-(3-Chloro-4-methylphenyl)-4-(3-pyridyl)thio-4,5-dihydro-3(2H)pyridazinone.
20. 6-(3-Bromo-4-methylphenyl)-4-(2-pyridyl)thio-4,5-dihydro-3(2H)pyridazinone.
21. 4-(2-Methylphenyl)thio-6-(3,4,5-trichlorophenyl)-4,5-dihydro-3(2H)pyridazinone.
22. 6-(3,5-Dichloro-4-methylphenyl)-4-methylthio-4,5-dihydro-3(2H)pyridazinone.
23. 6-(3,5-Dichloro-4-methylphenyl)-4-ethylthio-4,5-dihydro-3(2H)pyridazinone.
24. 6-(3,5-Dichloro-4-methylphenyl)-4-isopropylthio-4,5-dihydro-3(2H)pyridazinone.
25. 6-(3,5-Dichloro-4-methylphenyl)-4-(2-hydroxyethyl)-thio-4,5-dihydro-3(2H)pyridazinone.
26. 4-(2-Carboxyethyl)thio-6-(3,5-dichloro-4-methylphenyl)-4,5-dihydro-3(2H)pyridazinone.
27. 6-(3,5-Dichloro-4-methylphenyl)-4-ethoxycarbonylmethyl-thio-4,5-dihydro-3(2H)pyridazinone.
28. 6-(3,5-Dichloro-4-methylphenyl)-4-(2-methoxycarbonyl-ethyl)thio-4,5-dihydro-3(2H)pyridazinone.
29. 4-Allylthio-6-(3,5-dichloro-4-methylphenyl)-4,5-dihydro-3(2H)pyridazinone.
30. 6-(3,5-Dichloro-4-methylphenyl)-4-(4-nitrophenyl)thio-4,5-dihydro-3(2H)pyridazinone.
31. 4-Benzylthio-6-(3,5-dichloro-4-methylphenyl)-4,5-dihydro-3(2H)pyridazinone.
32. 4-Carboxymethylthio-6-(3,5-dichloro-4-methoxyphenyl)-4,5-dihydro-3(2H)pyridazinone.
33. 4-(4-Chlorobenzyl)thio-6-(3,5-dibromo-4-ethylphenyl)-4,5-dihydro-3(2H)pyridazinone.
34. 6-(3,5-Dibromo-4-methoxyphenyl)-4-hexylthio-4,5-dihydro-3(2H)pyridazinone.
35. 6-(3,5-Dibromo-4-ethoxyphenyl)-4-(4-methylbenzyl)-thio-4,5-dihydro-3(2H)pyridazinone.
36. 6-(3,5-Dibromo-4-methoxyphenyl)-4-methylthio-4,5-dihydro-3(2H)pyridazinone.
37. 4-Allylthio-6-(3-bromophenyl)-4,5-dihydro-3(2H)-pyridazinone.

The compounds of formula (VII) are in themselves valuable antifungal agents, or they may be used, as described in more detail hereafter, to prepare corresponding compounds of formula (VI), which also have valuable antifungal activity.

The process of the present invention is preferably carried out using one of the sequences of reactions hereinafter described as Methods A-D.

Method A

Compounds of formulae (VII) and, if desired, (VI) may be prepared by the reactions illustrated in the following reaction scheme.

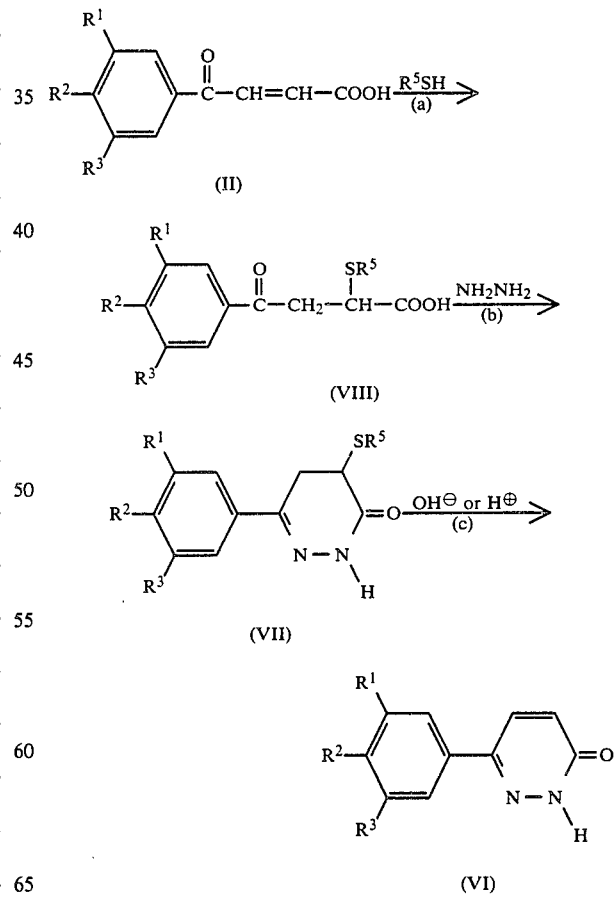

In the above reaction scheme, $R^1$, $R^2$, $R^3$ and $R^5$ are as hereinbefore defined.

Step (a) of this reaction scheme comprises reacting the 4-(substituted phenyl)-4-oxo-2-butenoic acid of formula (II) with a thiol of formula $R^5SH$ to give the corresponding 4-(substituted phenyl)-2-(substituted thio)-4-oxobutyric acid of formula (VIII). The nature of the thiol employed in this reaction will, of course, depend upon the nature of the group $R^5$ (which may be an optionally substituted alkyl group, a lower alkenyl group, an optionally substituted phenyl group, an optionally substituted aralkyl group or an optionally substituted pyridyl group) which it is desired to introduce into the compound of formula (VIII). Specific examples of such thiols include: lower alkanethiols, in which the alkane moiety may be unsubstituted or may have one or more hydroxy, lower alkoxy, carboxy or lower alkoxycarbonyl substituents, for example methanethiol, ethanethiol, butanethiol, thioglycolic acid, 3-mercaptopropionic acid, lower alkyl esters of these acids or mercaptoethanol; optionally substituted benzenethiols, such as benzenethiol, 4-methylbenzenethiol or 4-chlorobenzenethiol; optionally substituted aralkanethiols, such as phenylmethanethiol, 4-methylphenylmethanethiol or 4-chlorophenylmethanethiol; alkenethiols, such as 2-propene-1-thiol, 2-butene-1-thiol or 2-methyl-2-propene-1-thiol; or optionally substituted pyridinethiols, such as pyridine-2-thiol, pyridine-3-thiol, pyridine-4-thiol, 3-nitropyridine-2-thiol, 4-chloropyridine-2-thiol or 6-methylpyridine-3-thiol. Where the desired final product is a compound of formula (VI), the group $—SR^5$ is eliminated in step (c) and its nature is, therefore, not critical and a wide variety of groups may be employed as the group represented by $R^5$, especially alkyl, aralkyl, phenyl and pyridyl groups having substituents other than those recommended above. However, where the desired final product is a compound of formula (VII), the group $R^5$ remains in this compound and can have an effect upon the efficacy of the compound; in this case, where $R^5$ represents a substituted alkyl, aralkyl, phenyl or pyridyl group, the substituents are preferably chosen from those recommended above.

The reaction of step (a) may be effected by reacting the compound of formula (II) with the thiol $R^5SH$ preferably in an inert solvent. The molar ratio of the thiol to the compound of formula (II) is preferably at least 1:1 and a large excess of the thiol may be emloyed, if desired. There is no particular limitation on the nature of the solvent, provided that it does not adversely affect the reaction. Examples of suitable solvents include: aromatic hydrocarbons, such as benzene, toluene or xylene; ethers, such as diethyl ether, tetrahydrofuran or dioxane; alcohols, such as methanol, ethanol or isopropanol; amides, such as dimethylformamide; dimethyl sulphoxide; water; and mixtures of any two or more thereof. The preferred solvent is water or a mixture of water with at least one alcohol.

In order to promote the reaction, it is preferably effected in the presence of a base, for example: an alkali metal hydroxide, such as sodium hydroxide or potassium hydroxide; an alkali metal carbonate or bicarbonate, such as sodium carbonate, potassium carbonate or sodium bicarbonate; or a tertiary amine, such as triethylamine, triethylenediamine or pyridine.

There is no particular limitation on the reaction temperature, although, in order to prevent side reactions, the reaction is preferably effected at room temperature or with cooling. If the reaction is effected in the presence of a base, the resulting compound of formula (VIII) will normally be obtained in the form of the salt of the acid of formula (VIII) with that base; if desired, this salt may be converted to the free acid by treatment with an acid, although this is not essential.

Step (b) comprises reacting the compound of formula (VIII) with hydrazine to give the corresponding dihydropyridazinone compound of formula (VII).

The hydrazine is preferably employed in the form of its hydrate or of a salt with a mineral acid, such as hydrochloric acid or sulphuric acid. The reaction is preferably effected in the presence of an inert solvent, the nature of which is not critical, provided that it has no adverse effect upon the reaction. Examples of suitable solvents include: alcohols, such as methanol, ethanol or isopropanol; acetic acid; water; and mixtures of any two or more thereof. The preferred solvent is an alcohol or an aqueous alcohol. There is no particular limitation on the reaction temperature, and we therefore prefer to carry out the reaction at a temperature which may range from room temperature to the reflux temperature of the solvent employed; heating is preferred in order to promote the reaction.

Where the resulting compound of formula (VII) is the desired product, this may be separated from the reaction mixture by conventional means; otherwise, the compound of formula (VII), with or without separation from the reaction mixture, is subjected to the reaction of step (c).

In step (c), the compound of formula (VII) is treated with an acid or an alkali to give the desired compound of formula (VI).

The acid employed is preferably a mineral acid and examples include hydrochloric acid, sulphuric acid, nitric acid or phosphoric acid. The alkali employed is preferably an alkali metal hydroxide or carbonate, for example sodium hydroxide, potassium hydroxide, sodium carbonate or potassium carbonate. The amount of acid or alkali employed is preferably at least one equivalent per equivalent of compound of formula (VII), although a large excess may be employed, if desired.

This reaction is preferably effected in the presence of an inert solvent, the nature of which is not critical, provided it has no adverse effect on the reaction. Examples of such solvents include: alcohols, such as methanol, ethanol or isopropanol; ethers, such as dioxane or tetrahydrofuran; amides, such as dimethylformamide; dimethyl sulphoxide; water; or a mixture of any two or more thereof. Water or a mixture of water with at least one alcohol is preferably employed. There is no particular limitation on the reaction temperature, and the reaction is, therefore, preferably effected at a temperature from room temperature to the reflux temperature of the solvent employed; heating is preferred, in order to promote the reaction.

If desired, steps (b) and (c) may be effected in a single step by carrying out the reaction with hydrazine in the presence of at least one equivalent of hydrogen or hydroxyl ions per equivalent of the compound of formula (VIII).

After completion of the reaction, the compound of formula (VI) may be recovered by conventional means. However, it is a valuable characteristic of the present Method, as well as of Methods C and D, that the compound of formula (VI) can be obtained in the form of crystals simply by cooling the heated reaction mixture to room temperature and that the resulting crystals are of such high purity that no further purification, such as by recrystallisation, is required. The product may be collected by filtration and the mother liquor may be concentrated to give secondary crystals, which are also of such high purity that no further purification is required. This is, of course, an important commercial consideration, since it enables a purification step to be omitted, thus reducing both costs and the inevitable losses of final product.

In carrying out this Method, it is not necessary to isolate compound (VIII) or, if step (c) is to be carried out, compound (VII) and, if desired, all three steps can be carried out continuously, such a continuous operation being commercially advantageous. Step (c) of this Method regenerates the thiol $R^5SH$, which may be recovered and recycled to step (a), thus further reducing costs and improving the commercial value of this Method.

Method B

In this embodiment of the process of the invention, the reactions may be carried out as summarised in the following reaction scheme:

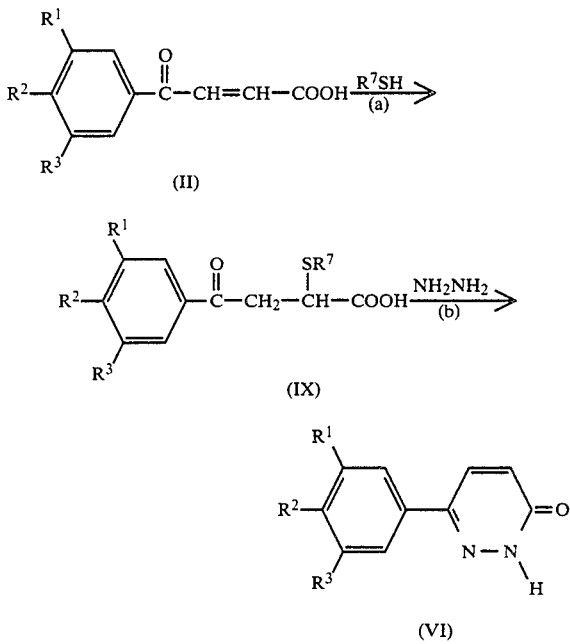

In the above formulae, $R^1$, $R^2$, $R^3$ and $R^7$ are as defined above, specifically, $R^7$ represents a group of formula

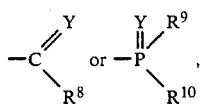

in which Y represents an oxygen or sulphur atom, $R^8$ and $R^9$ each represent a lower alkoxy group and $R^{10}$ represents a lower alkoxy group, a lower alkyl group or a phenyl group.

The first step (a) of the reaction comprises reacting the compound of formula (II) with a thiocarbonic, thiophosphoric or thiophosphonic ester $R^7SH$, to give the compound of formula (IX). The thiocarbonic ester is preferably used in the form of a salt, more preferably an alkali metal (e.g. potassium) salt. Where Y represents a sulphur atom, the thiocarbonic ester is an ester of dithiocarbonic acid, preferably potassium O-ethyl dithiocarbonate; where Y represents an oxygen atom, the ester is an ester of monothiocarbonic acid, e.g. potassium O-ethyl thiocarbonate.

Where $R^7$ represents a group of formula

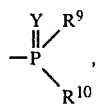

the compound of formula $R^7SH$ is a monothio- or dithio-phosphoric or phosphonic acid and specific examples of such compounds include: O,O-diethylthiophosphoric acid; O,O-dimethyldithiophosphoric acid; O,O-diethyldithiophosphoric acid; O,O-diisopropyldithiphosphoric acid; O,P-dimethyldithiophosphonic acid; and O-ethyl-P-phenyldithiophosphonic acid.

We prefer to employ equimolar amounts of the compound of formula (II) and the compound $R^7SH$ or to employ an excess of the compound $R^7SH$. The reaction is preferably effected in the presence of a solvent, the nature of which is not critical, provided that it has no adverse effect upon the reaction. Examples of solvents which may be employed include the solvents recommended for use in step (a) of Method A and ketones, such as acetone. Where the compound $R^7SH$ is a thiocarbonic ester, we prefer to use water as the solvent; where it is a thiophosphoric or thiophosphonic acid ester, we prefer to use an alcohol or a ketone as the solvent. The reaction is preferably effected at room temperature or below. When a thiocarbonic ester is used, the reaction mixture is preferably then treated with an acid to liberate the free acid of formula (IX), which is then used in step (b).

Step (b) comprises reacting the compound of formula (IX) with hydrazine to give the desired compound of formula (VI) directly. The hydrazine is preferably employed in the form of a hydrate and the reaction is preferably effected in the presence of an inert solvent, such as those recommended for use in step (b) of Method A. If desired, step (b) may be effected immediately after step (a) without any intermediate isolation of the compound of formula (IX). The reaction is preferably effected at room temperature or above.

Method C

In this embodiment, the process of the invention is effected as shown by the following reaction scheme:

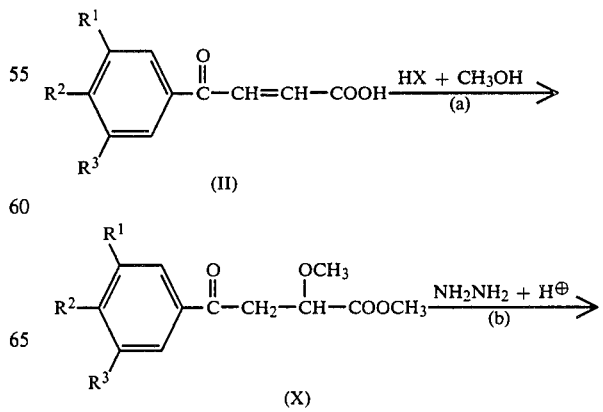

-continued

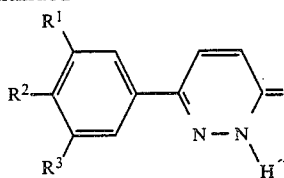

(VI)

In the formulae, $R^1$, $R^2$ and $R^3$ are as defined above and X represents a halogen atom.

Thus, step (a) of this Method comprises reacting the compound of formula (II) with a hydrogen halide in methanol, to give the compound of formula (X); this reaction comprises addition of methanol across the double bond of the compound of formula (II) and, because methanol is an alcohol, esterification of its carboxy group. Examples of hydrogen halides which may be employed in this reaction include hydrogen chloride and hydrogen bromide, of which we prefer hydrogen chloride. The hydrogen halide is preferably employed in a large excess relative to the compound of formula (II).

The reaction may be conducted in a mixed solvent containing the methanol, but we prefer that it should be effected simply by suspending the compound of formula (II) in methanol alone, the methanol serving as a solvent.

There is no particular limitation on the reaction temperature and the reaction may be conducted at temperatures ranging from ice-cool to the reflux temperature of the solvent employed.

As a result of a detailed inspection of the reaction by means of high-pressure liquid chromatography, it is believed that this reaction takes place in two stages: first, the compound of formula (II) is esterified, the hydrogen halide serving as catalyst, whilst the hydrogen halide is simultaneously added across the double bond to produce a corresponding methyl 4-(substituted phenyl)-2-halo-4-oxobutyrate; the halogen atom in this compound is then replaced by a methoxy group, to give the compound of formula (X).

Step (b) comprises reacting the compound of formula (X) with hydrazine in the presence of or followed by an acid, to give the compound of formula (VI) directly. This step, thus, corresponds to a combination of steps (b) and (c) of Method A. It is believed that the reaction proceeds via an intermediate corresponding to the compound of formula (VII) formed in Method A (but in which the group —$SR^5$ has been replaced by a methoxy group), but this intermediate is a little unstable and it is therefore desirable to produce the compound of formula (VI) directly without isolating the intermediate.

To carry out the reaction of step (b), the compound of formula (X) is first reacted with hydrazine in a suitable solvent, preferably with heating, after which an acid (in an amount which may range from equimolar to a large excess) is added and the heating is continued to give the compound of formula (VI). The hydrazine is preferably employed in the form of an acid salt. Alternatively, it is possible to add an acid to the reaction mixture together with the hydrazine. The acid may be a mineral acid, such as those exemplified for use with Method A, or an organic acid, such as acetic acid. We particularly prefer to carry out this reaction by heating the compound of formula (X) with hydrazine in acetic acid, the acetic acid also serving as a solvent.

Method D

In this embodiment of the process of the invention, the reactions may be carried out as illustrated by the following reaction scheme:

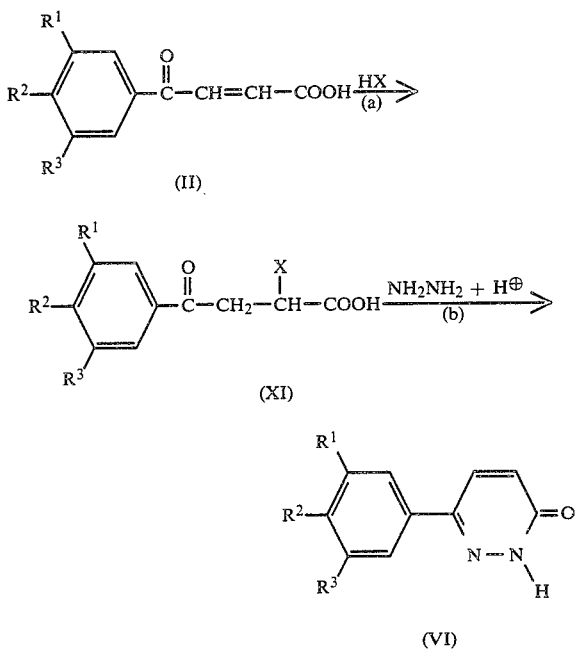

In the above formulae, $R^1$, $R^2$, $R^3$ and X are as defined above.

Step (a) of this Method comprises reacting the compound of formula (II) with a hydrogen halide, whereupon the hydrogen halide adds across the double bond of the compound (II). In this respect, the reaction is similar to the first stage of step (a) of Method C, although, in this case, the halo compound of formula (XI) is the desired product. The hydrogen halide employed in this reaction may be any of those described for use in step (a) of Method C and the amount of hydrogen halide employed may range from equimolar to a large excess with respect to the compound of formula (II).

The reaction is preferably effected in an inert solvent, the nature of which is not critical, provided that it has no adverse effect upon the reaction. Examples of suitable solvents include: ketones, such as acetone, methyl ethyl ketone or methyl isobutyl ketone; ethers, such as diethyl ether, dioxane or tetrahydrofuran; and halogenated hydrocarbons, such as methylene chloride, chloroform, ethylene dichloride or tetrachloroethane; of these, we particularly prefer ketones. The reaction temperature is also not critical and the reaction may be carried out at a temperature ranging from ice-cool to the reflux temperature of the solvent employed; the preferred reaction temperature is within the range from 5° to 20° C.

Step (b) of this Method comprises reacting the resulting compound of formula (XI) with hydrazine in the presence of or followed by an acid, to give the desired compound of formula (VI). The reaction conditions are similar to those described for step (b) of Method C, but, in this case, we prefer to use a mineral acid.

The compounds of formula (II), which are the starting materials for use in all of the above Methods are mostly known compounds. The preferred starting material of formula (II) is that in which $R^1$ and $R^3$ both represent chlorine atoms; whilst $R^2$ represents a methyl group. This may be prepared, in accordance with the method described in Japanese patent application Kokai (i.e. as laid open to public inspection) No. 36434/80, by chlorinating 4-(4-methylphenyl)-4-oxo-2-butenoic acid in the presence of at least 2.5 moles of anhydrous aluminium chloride per mole of the acid. This method, however, requires a large quantity of aluminium chloride, which thus adds to the cost of the method and gives rise to problems with treating waste water. Moreover, in addition to the desired dichloro compound, a large quantity of the corresponding trichloro compound is also produced in the chlorinating step and this by-product is difficult to remove.

Accordingly, the 4-(3,5-dichloro-4-methylphenyl)-4-oxo-2-butenoic acid employed as starting material in the present invention is preferably prepared by the process summarised in the following reaction scheme:

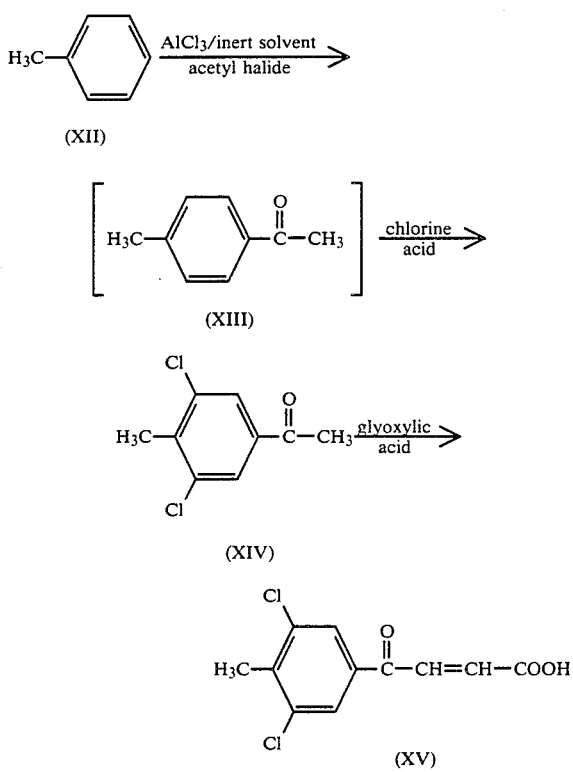

The first step of this process comprises reacting toluene, of formula (XII), with an acetyl halide in the presence of anhydrous aluminium chloride in an inert solvent, to prepare p-methylacetophenone (XIII), which is chlorinated, without intermediate isolation and then treated with an acid, to give 3,5-dichloro-4-methylacetophenone of formula (XIV).

An alternative process for preparing the compound of formula (XIV) is disclosed in J. Org. Chem., 23, 1412 (1958) and comprises conducting the chlorination by heating 4-methylacetophenone with 2.5 moles of aluminium chloride, per mole of 4-methylacetophenone, at 55° C. without a solvent; this, however, only gives a yield of 15% and gives the reaction product in the form of a solid, which makes recovery of the desired compound difficult.

Examples of acetyl halides which may be employed include acetyl chloride and acetyl bromide. The acetyl halide is preferably employed in an amount of from 1 to 1.5 moles per mole of toluene, whilst the anhydrous aluminium chloride is preferably employed in an amount of from 1.1 to 1.5 moles per mole of toluene. The reaction is carried out in an inert solvent, the nature of which is not critical, provided that it has no adverse effect upon the reaction; suitable solvents are halogenated hydrocarbons, such as ethylene dichloride, tetrachloroethane or trichloroethane. The reaction temperature is preferably from 0° to 10° C. The p-methylacetophenone thus produced is then subjected, without isolation, to chlorination, preferably at a temperature below 20° C., more preferably from 0° to 10° C., and the resulting complex is then decomposed by treatment with an acid, to give the desired 3,5-dichloro-4-methylacetophenone of formula (XIV). This process enables the compound of formula (XIV) to be obtained in a higher yield than can be achieved by the known method described above. Moreover, since the reaction mixture is a liquid, it is easy to decompose the complex compound by acid treatment after the reaction and the product is easy to obtain.

The second step of this process comprises reacting the compound of formula (XIV) with glyoxylic acid, to give the desired compound of formula (II). This reaction may be effected in the presence of a catalytic amount of acid, preferably acetic acid, as described in Japanese Patent Publication No. 39020/77.

The process of the present invention is further illustrated by the following Examples.

EXAMPLE 1

6-(3,5-Dichloro-4-methylphenyl)-4-methylthio-4,5-dihydro-3(2H)pyridazinone (a) Preparation of 3,5-dichloro-4-methylacetophenone from toluene 18.8 g (0.24 mole) of acetyl chloride were added dropwise, with ice-cooling and stirring, to a suspension of 34.7 g (0.26 mole) of anhydrous aluminium chloride powder in 150 ml of 1,2-dichloroethane. The mixture was stirred, with ice-cooling, for a further 30 minutes, after which 18.4 g (0.2 mole) of toluene were added dropwise, with stirring, over a period of about 20 minutes, whilst maintaining an internal temperature below 5° C. Stirring was continued for a further 1 hour, after which 23 ml of liquified chlorine, trapped in dry ice/acetone, were blown little by little over a period of 4 hours into this mixture, whilst maintaining it at an internal temperature of from 5° to 10° C. by ice-cooling. When the addition was complete, the mixture was stirred at 5°–10° C. for a further 30 minutes, after which the reaction mixture was poured into a mixture of 50 ml of concentrated hydrochloric acid and 500 g of broken ice. The mixture was then extracted with 500 ml of diethyl ether and the extract was washed with water and then dried over anhydrous sodium sulphate. The solvent was then distilled off, giving 47.9 g of a crude product, which was then subjected to column chromatography through silica gel, eluted with a 1:1 by volume mixture of hexane and benzene, to give 22.8 g (yield 56.1%) of the desired 3,5-dichloro-4-methylacetophenone, melting at 64°–66° C. and boiling at 108°–111° C./400 Pa (3 mmHg).

Elemental analysis: Calculated for $C_9H_8OCl_2$: C, 53.24%; H, 3.97%; Cl, 34.92%. Found: C, 53.69%; H, 3.87%; Cl, 35.03%.

Infrared Absorption Spectrum (Nujol-trade markmull) $\nu_{max}cm^{-1}$: 1690.

Nuclear Magnetic Resonance Spectrum ($CCl_4$) δ ppm: 2.50 (6H, singlet, methyl); 7.77 (2H, singlet, phenyl).

(b) Preparation of 4-(3,5-dichloro-4-methylphenyl)-4-oxo-2-butenoic acid from 3,5-dichloro-4-methylacetophenone 10.2 g (0.1 mole) of acetic anhydride were added to 9.3 g (0.1 mole) of glyoxylic acid monohydrate and the mixture was heated, with stirring, on an oil bath at 60° C. for 10 minutes to obtain a homogeneous solution. To this solution were added, in turn, 20.3 g (0.1 mole) of 3,5-dichloro-4-methylacetophenone, prepared as described in step (a) above, 28.8 g of acetic acid and a catalytic amount (300 mg) of concentrated sulphuric acid, whilst ice-cooling. The mixture was then heated, with stirring, on an oil bath at 105°–110° C. for 2 hours, after which it was cooled and 100 ml of diisopropyl ether were added. The mixture was stirred and the resulting crystals were collected by filtration and washed first with water and then with a small amount of diisopropyl ether, after which they were dried to give 20.8 g (yield 80.3%) of the desired 4-(3,5-dichloro-4-methylphenyl)-4-oxo-2-butenoic acid, melting at 206°–216° C.

(c) Preparation of 4-(3,5-dichloro-4-methylphenyl)-2-methylthio-4-oxobutyric acid from 4-(3,5-dichloro-4-methylphenyl)-4-oxo-2-butenoic acid 2.59 g (0.01 mole) of 4-(3,5-dichloro-4-methylphenyl)-4-oxo-2-butenoic acid, prepared as described in step (b) above, were suspended in 10 ml of water, and then 3.5 g (0.01 mole) of a 20% w/v aqueous solution of sodium methanethiolate were poured into the suspension, whilst water-cooling and stirring. The mixture was then stirred for a further 30 minutes, after which 2 ml of concentrated hydrochloric acid were added dropwise to the mixture, whilst water-cooling, and the resulting crystals were collected by filtration, washed with water and air-dried, to give 3.03 g (yield 98.7%) of the desired 4-(3,5-dichloro-4-methylphenyl)-2-methylthio-4-oxobutyric acid, melting at 158°–160° C.

Elemental Analysis: Calculated for $C_{12}H_{12}O_3Cl_2S$: C, 46.88%; H, 3.91%; Cl, 23.11%; S, 10.42%. Found: C, 47.11%; H, 3.53%; Cl, 23.04%; S, 10.51%.

Infrared Absorption Spectrum (Nujol mull) $\nu_{max}cm^{-1}$: 2400–2700, 1720, 1690.

Nuclear Magnetic Resonance Spectrum (heptadeuterated dimethylformamide) δ ppm: 2.30 (3H, singlet, methyl); 2.53 (3H, singlet, methylthio); 3.12–4.12 (3H, multiplet, methylene and methine); 7.42 (1H, broad singlet, carboxy); 8.13 (2H, singlet, phenyl).

Following the same procedure as described above, the following compounds were also prepared:
(i) 4-(3-Bromophenyl)-2-methylthio-4-oxobutyric acid, melting at 123°–134° C.
(ii) 4-(3-Bromophenyl)-2-ethylthio-4-oxobutyric acid, melting at 125°–134° C.
(iii) 4-(3-Bromophenyl)-2-isopropylthio-4-oxobutyric acid, melting at 136°–138° C.
(iv) 4-(3-Bromophenyl)-2-(2-hydroxyethyl)thio-4-oxobutyric acid, in the form of an oil.
(v) 4-(3-Bromophenyl)-2-(2'-carboxyethyl)thio-4-oxobutyric acid, melting at 135°–137° C.
(vi) 4-(3-Bromophenyl)-2-phenylthio-4-oxobutyric acid, melting at 125°–128° C.
(vii) 4-(3-Bromophenyl)-2-(3-nitro-2-pyridyl)thio-4-oxobutyric acid, melting at 159°–162° C.
(viii) 4-(4-Methoxyphenyl)-2-methylthio-4-oxobutyric acid, melting at 116°–118° C.
(ix) 4-(3,4-Dichlorophenyl)-2-methylthio-4-oxobutyric acid, melting at 136°–139° C.
(x) 4-(3,4-Dichlorophenyl)-2-ethylthio-4-oxobutyric acid, melting at 108°–110° C.
(xi) 4-(3,4-Dichlorophenyl)-2-isopropylthio-4-oxobutyric acid, melting at 136°–138° C.
(xii) 4-(3,4-Dichlorophenyl)-2-(2-hydroxyethyl)thio-4-oxobutyric acid, melting at 110°–112° C.
(xiii) 2-(2-Carboxyethyl)thio-4-(3,4-dichlorophenyl)-4-oxobutyric acid, melting at 150°–152° C.
(xiv) 4-(3-Bromo-4-chlorophenyl)-2-methylthio-4-oxobutyric acid, melting at 143°–145° C.
(xv) 4-(3,5-Dichloro-4-methylphenyl)-2-ethylthio-4-oxobutyric acid, melting at 168°–172° C.
(xvi) 4-(3,5-Dichloro-4-methylphenyl)-2-isopropylthio-4-oxobutyric acid, melting at 166°–169° C.
(xvii) 4-(3,5-Dichloro-4-methylphenyl)-2-(2-hydroxyethyl)-thio-4-oxobutyric acid, melting at 129°–131° C.
(xviii) 2-(2-Carboxyethyl)thio-4-(3,5-dichloro-4-methylphenyl)-4-oxobutyric acid, melting at 149°–151° C.
(xix) 4-(3,5-Dichloro-4-methylphenyl)-2-ethoxycarbonylmethylthio-4-oxobutyric acid, melting at 95°–97° C.
(xx) 4-(3,5-Dichloro-4-methylphenyl)-2-(2-methoxycarbonyl-ethyl)thio-4-oxobutyric acid, melting at 125°–127° C.
(xxi) 2-Benzylthio-4-(3,5-dichloro-4-methylphenyl)-4-oxobutyric acid, melting at 132°–135° C.
(xxii) 4-(3,5-Dibromo-4-methoxyphenyl)-2-hexylthio-4-oxobutyric acid, melting at 103°–105° C.
(xxiii) 2-Allylthio-4-(3-bromophenyl)-4-oxobutyric acid, melting at 50°–63° C.

(d) Preparation of 6-(3,5-dichloro-4-methylphenyl)-4-methylthio-4,5-dihydro-3(2H)pyridazinone (Compound No. 22) from 4-(3,5-dichloro-4-methylphenyl)-2-methylthio-4-oxobutyric acid 1.54 g (0.005 mole) of 4-(3,5-dichloro-4-methylphenyl)-2-methylthio-4-oxobutyric acid, prepared as described in step (c) above, were suspended in 5 ml of ethanol and then 0.25 g of hydrazine monohydrate was added, at room temperature, to the suspension, after which the mixture was stirred for 1 hour at room temperature. The mixture was then heated under reflux for 6 hours, after which it was cooled and the resulting crystals were collected by filtration and washed with a small amount of ethanol, to give 1.32 g (yield 87.1%) of the desired Compound No. 22, melting at 163°–165° C.

Elemental analysis: Calculated for $C_{12}H_{12}ON_2Cl_2S$: C, 47.54%; H, 3.99%; N, 9.24%; Cl, 23.31%; S, 10.57%. Found: C, 47.54%, H, 3.63%; N, 9.15%, Cl, 23.68%; S, 10.51%.

Infrared Absorption Spectrum (Nujol mull) $\nu_{max}cm^{-1}$: 3200, 3100, 2000–2800, 1680, 1610.

Nuclear Magnetic Resonance Spectrum (deuterochloroform) δ ppm: 2.23 (3H, singlet, methyl); 2.52 (3H, singlet, methylthio); 3.19 (2H, doublet, J=6 Hz, methylene); 3.58 (1H, doubled doublet, J=6 Hz, methine); 7.78 (2H, singlet, phenyl); 9.72 (1H, broad singlet, NH).

Following the procedure described above, the following compounds were also prepared, starting with the corresponding compounds prepared as described in step (c) above:

(i) 6-(3-Bromophenyl)-4-methylthio-4,5-dihydro-3(2H)pyridazinone, melting at 151°–152° C. (Compound No. 1).

(ii) 6-(3-Bromophenyl)-4-ethylthio-4,5-dihydro-3(2H)pyridazinone, melting at 126°–129° C. (Compound No. 2).

(iii) 6-(3-Bromophenyl)-4-isopropylthio-4,5-dihydro-3(2H)pyridazinone, melting at 155°–158° C. (Compound No. 3).

(iv) 6-(3-Bromophenyl)-4-(2-hydroxyethyl)thio-4,5-dihydro-3(2H)pyridazinone, melting at 115°–118° C. (Compound No. 4).

(v) 6-(3-Bromophenyl)-4-(2-carboxyethyl)thio-4,5-dihydro-3(2H)pyridazinone, melting at 150°–152° C. (Compound No. 5).

(vi) 6-(3-Bromophenyl)-4-phenylthio-4,5-dihydro-3(2H)pyridazinone, melting at 153°–156° C. (Compound No. 6).

(vii) 6-(3-Bromophenyl)-4-(3-nitro-2-pyridyl)thio-4,5-dihydro-3(2H)pyridazinone, melting at 171°–174° C. (Compound No. 7).

(viii) 6-(4-Methoxyphenyl)-4-methylthio-4,5-dihydro-3(2H)pyridazinone, melting at 145°–147° C. (Compound No. 9).

(ix) 6-(3,4-Dichlorophenyl)-4-methylthio-4,5-dihydro-3(2H)pyridazinone, melting at 149°–152° C. (Compound No. 10).

(x) 6-(3,4-Dichlorophenyl)-4-ethylthio-4,5-dihydro-3(2H)pyridazinone, melting at 134°–136° C. (Compound No. 11).

(xi) 6-(3,4-Dichlorophenyl)-4-isopropylthio-4,5-dihydro-3(2H)pyridazinone, melting at 136°–138° C. (Compound No. 12).

(xii) 6-(3,4-Dichlorophenyl)-4-(2-hydroxyethyl)thio-4,5-dihydro-3(2H)pyridazinone, melting at 127°–129° C. (Compound No. 13).

(xiii) 4-(2-Carboxyethyl)thio-6-(3,4-dichlorophenyl)-4,5-dihydro-3(2H)pyridazinone, melting at 162°–165° C. (Compound No. 14).

(xv) 6-(3,5-Dichloro-4-methylphenyl)-4-ethylthio-4,5-dihydro-3(2H)pyridazinone, melting at 174°–177° C. (Compound No. 23).

(xvi) 6-(3,5-Dichloro-4-methylphenyl)-4-isopropylthio-4,5-dihydro-3(2H)pyridazinone, melting at 174°–177° C. (Compound No. 24).

(xvii) 6-(3,5-Dichloro-4-methylphenyl)-4-(2-hydroxyethyl)thio-4,5-dihydro-3(2H)pyridazinone, melting at 192°–195° C. (Compound No. 25).

(xviii) 4-(2-Carboxyethyl)thio-6-(3,5-dichloro-4-metylphenyl)-4,5-dihydro-3(2H)pyridazinone, melting at 192°–194° C. (Compound No. 26).

(xix) 6-(3,5-Dichloro-4-methylphenyl)-4-ethoxycarbonylmethylthio-4,5-dihydro-3(2H)pyridazinone, melting at 146°–149° C. (Compound No. 27).

(xx) 6-(3,5-Dichloro-4-methylphenyl)-4-(2-methoxycarbonylethyl)thio-4,5-dihydro-3(2H)pyridazinone, melting at 126°–128° C. (Compound No. 28).

(xxi) 4-Benzylthio-6-(3,5-dichloro-4-methylphenyl)-4,5-dihydro-3(2H)pyridazinone, melting at 161°–163° C. (Compound No. 31).

(xxii) 6-(3,5-Dibromo-4-methoxyphenyl)-4-hexylthio-4,5-dihydro-3(2H)pyridazinone, melting at 80°–83° C. (Compound No. 34).

(xxiii) 4-Allylthio-6-(3-bromophenyl)-4,5-dihydro-3(2H)pyridazinone, melting at 112°–115° C. (Compound No. 37).

EXAMPLE 2

Preparation of 6-(3,5-dichloro-4-methylphenyl)-3(2H)pyridazinone from 6-(3,5-dichloro-4-methylphenyl)-4-methylthio-4,5-dihydro-3(2H)pyridazinone A mixture of 6.06 g (0.02 mole) of 6-(3,5-dichloro-4-methylphenyl)-4-methylthio-4,5-dihydro-3(2H)pyridazinone, prepared as described in Example 1(d), 20 ml of water and 5.2 ml of concentrated hydrochloric acid was heated under reflux for 2 hours. The mixture was then cooled and the resulting crystals were collected by filtration, air-dried, washed with a small amount of ethyl acetate and again air-dried, to give 4.59 g (yield 90%) of the desired 6-(3,5-dichloro-4-methylphenyl)-3(2H)pyridazinone, melting at 254°–258° C.

EXAMPLE 3

Preparation of 6-(3,5-dichloro-4-methylphenyl)-3(2H)pyridazinone from 4-(3,5-dichloro-4-methylphenyl)-4-oxo-2-butenoic acid 7 g of a 20% w/v aqueous solution of sodium methanethiolate were poured into a suspension of 5.18 g (0.02 mole) of 4-(3,5-dichloro-4-methylphenyl)-4-oxo-2-butenoic acid, prepared as described in Example 1(b), in 20 ml of water, whilst water-cooling; the mixture was then stirred for 30 minutes. To the resulting mixture were added, whilst water-cooling, 2.08 ml (0.02 mole) of concentrated hydrochloric acid, after which the mixture was stirred. 1.1 g of hydrazine monohydrate was then added, with water-cooling, to the mixture, after which the mixture was stirred at room temperature for 1 hour, and then heated under reflux for 2 hours. At the end of this time, 5.2 ml (0.04 mole) of concentrated hydrochloric acid were added and the mixture was further heated under reflux for 1.5 hours. After the mixture had been cooled, the resulting crystals were collected by filtration, washed with water and air-dried, to give 4.97 g (crude yield 97.5%) of the desired product, melting at 243°–249° C. This product was washed with a small amount of ethyl acetate and then air-dried, to give 3.90 g (yield 76.5%) of the desired product in pure form, melting at 254°–258° C.

EXAMPLE 4

6-(3,5-Dichloro-4-methylphenyl)-3(2H)pyridazinone (a) Preparation of methyl 4-(3,5-dichloro-4-methylphenyl)-2-methoxy-4-oxobutyrate from 4-(3,5-dichloro-4-methylphenyl)-4-oxo-2-butenoic acid 5.18 g (0.02 mole) of 4-(3,5-dichloro-4-methylphenyl)-4-oxo-2-butenoic acid, prepared as described in Example 1(b), were suspended in 50 ml of methanol and the suspension was then saturated with dry hydrogen chloride gas by blowing the gas through the suspension whilst ice-cooling and stirring it. The resulting mixture was then stirred at room temperature for a further 2 hours, to give methyl 2-chloro-4-(3,5-dichloro-4-methylphenyl)-4-oxobutyrate. The resulting mixture was then heated under reflux for a further 2 hours to replace the chlorine substituent at the 2-position by a methoxy group. After completion of this reaction, methanol was distilled off and the residue was extracted with diethyl ether. The extract was washed with water and then dried over anhydrous sodium sulphate. The solvent was then distilled off, giving 5.93 g of a crude product, which was subjected to column chromatography through silica gel, eluted successively with benzene and then with a 20:1 by volume mixture of benzene and ethyl acetate, to give 4.46 g (yield 73.1%) of the desired methyl 4-(3,5-dichloro-4-methylphenyl)-2-methoxy-4-oxobutyrate, melting at 75°–78° C.

Elemental analysis: Calculated for $C_{13}H_{14}O_4Cl_2$: C, 51.17%; H, 4.62%; Cl, 23.24%. Found: C, 51.00%; H, 4.38%; Cl, 23.45%.

Infrared Absorption Spectrum (Nujol mull) $\nu_{max}cm^{-1}$: 1740, 1675.

Nuclear Magnetic Resonance Spectrum (deuterochloroform) δ ppm: 2.50 (3H, singlet, methyl); 3.05–3.75 (2H, multiplet, methylene); 3.55 (3H, singlet, methoxy); 3.80 (3H, singlet, methoxycarbonyl); 4.40 (1H, doubled doublet, J=6 Hz, methine); 7.77 (2H, singlet, phenyl).

(b) Preparation of
6-(3,5-dichloro-4-methylphenyl)-3(2H)-pyridazinone from methyl 4-(3,5-dichloro-4-methylphenyl)-2-methoxy-4-oxobutyrate A mixture of 3.05 g (0.01 mole) of methyl 4-(3,5-dichloro-4-methylphenyl)-2-methoxy-4-oxobutyrate, 0.6 g (0.012 mole) of hydrazine monohydrate and 30 ml of methanol was heated under reflux for 3.5 hours. 1.1 ml of concentrated hydrochloric acid was then added to the mixture, after which it was again heated under reflux for a further 6 hours. At the end of this time, the solvent was distilled off and the residue was washed, in turn, with water and with a small amount of diethyl ether, after which it was dried to give 1.80 g of the desired product. The washings were extracted with ethyl acetate and the extract was dried over anhydrous sodium sulphate, after which the organic solvent was distilled off. The residue was washed in turn with benzene and with diethyl ether, to give a further 0.11 g of the desired product. The total yield of 6-(3,5-dichloro-4-methylphenyl)-3(2H)pyridazinone was 1.91 g (74.9%) and the properties of the product were identical with those of the products of Examples 1(d), 2 and 3.

EXAMPLE 5

Preparation of
6-(3,5-dichloro-4-methylphenyl)-3(2H)pyridazinone from methyl 4-(3,5-dichloro-4-methylphenyl)-2-methoxy-4-oxobutyrate 1.53 g (0.005 mole) of methyl 4-(3,5-dichloro-4-methylphenyl)-2-methoxy-4-oxobutyrate were added to 4 ml of acetic acid and the mixture was heated to form a solution, to which was then added 0.275 g (0.0055 mole) of hydrazine monohydrate. The mixture was heated under reflux for 3 hours and then cooled, after which it was diluted with 40 ml of water and stirred. The resulting crystals were collected by filtration, washed successively with water and with a small amount of ethyl acetate and then air-dried, to give 1.1 g (yield 86.2%) of the desired 6-(3,5-dichloro-4-methylphenyl)-3(2H)pyridazinone, having properties the same as those of the preceding Examples.

EXAMPLE 6

6-(3,5-Dichloro-4-methylphenyl)-3(2H)pyridazinone (a) Preparation of
2-chloro-4-(3,5-dichloro-4-methylphenyl)-4-oxobutyric acid from 4-(3,5-dichloro-4-methylphenyl)-4-oxo-2-butenoic acid A suspension of 5.18 g (0.02 mole) of 4-(3,5-dichloro-4-methylphenyl)-4-oxo-2-butenoic acid, prepared as described in Example 1(b), in 50 ml of methyl isobutyl ketone was saturated with dry hydrogen chloride gas, by blowing the gas through the suspension whilst ice-cooling and stirring it. The mixture was then stirred at room temperature for a further 1 hour, after which it was diluted with 30 ml of cold water and extracted with ethyl acetate. The extract was washed with water and then dried over anhydrous sodium sulphate, after which the solvent was distilled off and the residue was washed with a small amount of hexane and then dried, giving 5.91 g (yield 100%) of the desired 2-chloro-4-(3,5-dichloro-4-methylphenyl)-4-oxobutyric acid, melting at 129°–132° C.

Elemental analysis: Calculated for $C_{11}H_9O_3Cl_3$: C, 44.70%; H, 3.07%; Cl, 35.99%. Found: C, 44.73%; H, 3.26%; Cl, 35.78%.

Infrared Absorption Spectrum (Nujol mull) $\nu_{max}cm^{-1}$: 2400–2800, 1720, 1685.

Nuclear Magnetic Resonance Spectrum (deuterochloroform) δ ppm: 2.54 (3H, singlet, methyl); 3.65, 3.70 (2H, doublet, J=6 Hz, doublet, J=8 Hz, methylene); 4.80 (1H, doubled doublet, J=6 & 8 Hz, methine); 7.88 (2H, singlet, phenyl); 10.06 (1H, broad singlet, carboxy).

(b) Preparation of
6-(3,5-dichloro-4-methylphenyl)-3(2H)pyridazinone from 2-chloro-4-(3,5-dichloro-4-methylphenyl)-4-oxobutyric acid 1.48 g (0.005 mole) of 2-chloro-4-(3,5-dichloro-4-methylphenyl)-4-oxobutyric acid, prepared as described in step (a) above, were dissolved in a solution of 0.68 g (0.01 mole) of hydrazine hydrochloride in 15 ml of ethanol and 2 ml of water; the solution was then heated under reflux for 3 hours, after which it was cooled. The solvent was then distilled off and 20 ml of water were added to the residue. The mixture was stirred and the resulting crystals were collected by filtration, washed successively with water and with a small amount of diethyl ether and then dried, giving 0.85 g (yield 66.7%) of the desired 6-(3,5-dichloro-4-methylphenyl)-3(2H)pyridazinone, having the same properties as the product obtained in the preceding Examples.

EXAMPLE 7

Preparation of
6-(3,5-dichloro-4-methylphenyl)-3(2H)pyridazinone from 6-(3,5-dichloro-4-methylphenyl)-4-methylthio-4,5-dihydro-3(2H)pyridazinone (Compound No. 22)

A suspension of 1.52 g (0.005 mole) of 6-(3,5-dichloro-4-methylphenyl)-4-methylthio-4,5-dihydro-3(2H)-pyridazinone, prepared as described in Example 1(d), in 30 ml of 1N aqueous sodium hydroxide was refluxed for 1 hour. The reaction mixture was allowed to cool and then acidified by adding concentrated hydrochloric acid, whilst water-cooling. The crystals which precipitated were collected by filtration, thoroughly washed with water and then dried to give 1.2 g (yield 94%) of the desired 6-(3,5-dichloro-4-methylphenyl)-3(2H)pyridazinone, melting at 254°–258° C.

Following various of the methods described in the foregoing Examples, the following compounds were also prepared:

6-(3-Bromophenyl)-3(2H)pyridazinone, melting at 202°–204° C.;
6-(3,4-Dichlorophenyl)-3(2H)pyridazinone, melting at 258°–262° C.;
6-(3-Bromo-4-chlorophenyl)-3(2H)pyridazinone, melting at 289°–293° C.;
6-(4-Methoxyphenyl)-3(2H)pyridazinone, melting at 189°–192° C.

EXAMPLE 8

(a) Preparation of 4-(3-bromophenyl)-2-diethoxyphosphinothioylthio-4-oxobutanoic acid from 4-(3-bromophenyl)-4-oxo-2-butenoic acid 1.12 g (0.006 mole) of O,O-diethyldithiophosphoric acid were added dropwise to a solution of 1.28 g (0.005 mole) of 4-(3-bromophenyl)-4-oxo-2-butenoic acid in 20 ml of acetone, and then the mixture was stirred overnight at room temperature. At the end of this time, the solvent was distilled off and the residue was extracted with diethyl ether. The extract was washed with water and dried over anhydrous sodium sulphate, after which the solvent was distilled off. The residue was subjected to column chromatography through silica gel, eluted with a 4:1 by volume mixture of benzene and ethyl acetate. The resulting solid was recrystallised from a mixture of benzene and hexane, to give 1.54 g (yield 69.8%) of the desired 4-(3-bromophenyl)-2-diethoxyphosphinothioylthio-4-oxobutenoic acid, melting at 107°–111° C.

Infrared Absorption Spectrum (Nujol mull) $\nu_{max}$cm$^{-1}$: 2050–2800, 1750, 1680, 1010, 960.

Nuclear Magnetic Resonance Spectrum (deuterochloroform) δ ppm: 1.37 (6H, triplet, 2 methyl groups); 3.6–3.8 (2H, multiplet, methylene); 3.9–4.7 (5H, multiplet, 2 methylene groups and methine); 7.2–8.1 (4H, multiplet, phenyl); 8.90 (1H, singlet, carboxy).

Following the same procedure as described above, the following compounds were also prepared:
4-(3-Bromophenyl)-2-diisopropoxyphosphinothioylthio-4-oxobutanoic acid, melting at 106°–112° C.;
4-(3,5-Dichloro-4-methylphenyl)-2-diethoxyphosphinothioylthio-4-oxobutanoic acid, melting at 97°–99° C.;
Methyl 4-(3,5-dichloro-4-methylphenyl)-2-diethoxyphosphinothioylthio-4-oxobutanoate, $n_D^{25}$=1.5604;
4-(3,4-Dichlorophenyl)-2-diethoxyphosphinothioylthio-4-oxobutanoic acid, melting at 136°–137° C.

These compounds may then be used to prepare the corresponding pyridazinone derivatives of formula (I) by following essentially the same procedure as described in the second part of following step (b). However, as is described in step (b) we prefer to carry out preparation of the pyridazinone derivative directly from corresponding 4-oxo-2-butanoic acid, without intermediate isolation of the phosphinothioylthio derivative.

(b) Preparation of 6-(3-bromophenyl)-3(2H)pyridazinone from 4-(3-bromophenyl)-4-oxo-2-butenoic acid 1.12 g (0.006 mole) of O,O-diethyldithiophosphoric acid were added, at room temperature, to a suspension of 1.28 g of 4-(3-bromophenyl)-4-oxo-2-butenoic acid in 10 ml of ethanol, and then the mixture was stirred for 10 minutes. Formation of 4-(3-bromophenyl)-2-diethoxyphosphinothioylthio-4-oxobutanoic acid was confirmed by thin layer chromatography but the compound was not separated from the reaction mixture. 0.3 g (0.006 mole) of hydrazine monohydrate was added to the reaction mixture, which was then stirred overnight at room temperature. At the end of this time, the crystals which had precipitated were collected by filtration and washed with ethanol to give 0.48 g of the desired 6-(3-bromophenyl)-3(2H)pyridazinone. The filtrate was concentrated and then subjected to column chromatography through silica gel eluted with a 4:1 by volume mixture of benzene and ethyl acetate, to give a further 0.48 g of the product, a total of 0.96 g (yield 76%) of the product, melting at 202°–204° C.

EXAMPLE 9

(a) Preparation of 4-(3,5-dichloro-4-methylphenyl)-2-ethoxythiocarbonylthio-4-oxobutanoic acid from 4-(3,5-dichloro-4-methylphenyl)-4-oxo-2-butenoic acid A suspension of 2.59 g (0.01 mole) of 4-(3,5-dichloro-4-methylphenyl)-4-oxo-2-butenoic acid and 1.60 g (0.01 mole) of potassium O-ethyl dithiocarbonate in 40 ml of water was stirred at room temperature for 3 hours. At the end of this time, the mixture was ice-cooled, acidified by the addition of concentrated hydrochloric acid and then extracted with diethyl ether. The extract was subjected to column chromatography through silica gel, to give 3.60 g (yield 94.5%) of the desired 4-(3,5-dichloro-4-methylphenyl)-2-ethoxythiocarbonylthio-4-oxobutenoic acid, melting at 126°–128° C.

Infrared Absorption Spectrum (Nujol mull) $\nu_{max}$cm$^{-1}$: 2100–2750, 1700, 1690.

Nuclear Magnetic Resonance Spectrum (deuterochloroform) δ ppm: 1.42 (3H, triplet, J=7 Hz, methyl); 2.50 (3H, singlet, methyl); 3.64 (2H, doublet, J=6 Hz, COCH$_2$); 4.68 (2H, quartet, J=7 Hz, methylene); 5.03 (1H, triplet, J=6 Hz, methine); 7.82 (2H, singlet, phenyl); 9.40 (1H, broad singlet, carboxy).

(b) Preparation of 6-(3,5-dichloro-4-methylphenyl)-3(2H)-pyridazinone from 4-(3,5-dichloro-4-methylphenyl)-2-ethoxythiocarbonylthio-4-oxobutanoic acid 0.275 g (0.0055 mole) of hydrazine monohydrate was added to a solution of 1.91 g (0.005 mole) of 4-(3,5-dichloro-4-methylphenyl)-2-ethoxythiocarbonylthio-4-oxobutanoic acid, prepared as described in step (a) above, in 20 ml of ethanol, and the resulting mixture was refluxed for 3 hours. It was then cooled and the crystals which precipitated were collected by filtration and washed with ethanol, to give the desired product melting at 254°–258° C.

The ethanol washings were concentrated and the residue was subjected to column chromatography through silica gel, to give 6-(3,5-dichloro-4-methylphenyl)-4-mercapto-4,5-dihydro-3(2H)pyridazinone, melting at 184°–187° C.

The 6-(3,5-dichloro-4-methylphenyl)-3(2H)pyridazinone, in the form in which it is prepared by the majority of the above Examples shows an absorption, on infrared spectroscopy, at 1075 cm$^{-1}$, which is assigned to the carbonyl group, and has a powdery crystal form. However, when the compound is recrystallised from N,N-dimethylformamide, its form changes to crystalline needles and the infrared absorption also changes to 1680 and 1660 cm$^{-1}$, also assigned to the carbonyl group. However, the compound in both forms shows identical behaviour with respect to melting point, thin layer chromatography, high performance liquid chromatography and nuclear magnetic resonance spectrometry and it is thus concluded that they are both the same compound.

The novel compounds of formula (VII), like the known compounds of formula (VI) have effective antifungal activity and can be employed as agricultural fungicides, showing a preventive and curative effect against plant diseases, without damaging the host plants. Specifically, the compounds of the invention are effective in the control of sheath blight, which is a very serious disease attacking rice plants; for this use, they are preferably employed in the form of a foliar or surface spray. The compounds also effectively control damping-off, which is a disease caused by pathogenic fungi of the class Rhizoctonia and which attacks various plants, including sugar beet, cotton plants, cucumbers, melons and plants of the gourd family. Moreover, the compounds can be used to control stem rot, a disease caused by pathogenic fungi of the class Corticium, which attacks eggplants and cucumbers.

At effective doses, the compounds of the invention do not exhibit any phytotoxicity to such plants as rice plants, tomato plants, potatoes, cotton plants, aubergine plants, cucumbers and kidney beans. Moreover, they may be used effectively as fungicides in orchards, non-crop land and forests.

The compounds of the invention may be formulated as preparations of the type commonly employed as agricultural fungicides, for example powdery dusts, coarse dusts, fine granules, coarse granules, wettable powders, emulsifiable concentrates, aqueous liquids, water-soluble powders and oil suspensions, by mixing them with a carrier and, if required, with other auxiliary agents. The carrier employed may be natural or synthetic and organic or inorganic; it is mixed with the active compound to assist that compound to reach the material to be treated and to make it easier to store, transport or handle the active compound.

Suitable solid carriers are: inorganic substances, such as clays (examples of which are kaolinite, montmorillonite or attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes, such as carnauba wax and beeswax; or urea.

Examples of suitable liquid carriers are: paraffinic or naphthenic hydrocarbons, such as kerosine, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o-chlorotoluene; ethers, such as dioxane and tetrahydrofuran; ketones, such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol monoethyl ether, ethylene glycol monophenyl ether, diethylene glycol monoethyl ether and diethylene glycol monobutyl ether; polar solvents, such as dimethylformamide and dimethyl sulphoxide; and water.

The fungicidal compositions of the present invention may contain surface active agents to emulsify, disperse, wet, spread, bind, control disintegration of, improve fluidity of or rust-proof the fungicidal composition or to stabilize the active compound; although any of the conventional classes of surface active agent, be they non-ionic, anionic, cationic or amphoteric, may be employed, we prefer to employ non-ionic and/or anionic surface active agents. Examples of suitable non-ionic surface active agents are: the polymerization adducts of ethylene oxide with higher alcohols, such as lauryl alcohol, stearyl alcohol or oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di-alkylphosphoric acids, such as stearylphosphoric acid or dilaurylphosphoric acid; the polymerization adducts of ethylene oxide with amines, such as dodecylamine; the polymerization adducts of ethylene oxide with higher fatty acid amides, such as stearamide; the polymerization adducts of ethylene oxide with higher fatty acid esters of polyhydric alcohols, such as sorbitan, and said fatty acid esters themselves; and the polymerization adducts of ethylene oxide with propylene oxide.

Examples of suitable anionic surface active agents are: alkyl sulphate salts, such as sodium lauryl sulphate or oleyl sulphate amine salt; alkyl sulphonate salts, such as sodium dioctyl sulphosuccinate or sodium 2-ethylhexene sulphonate; and aryl sulphonate salts, such as sodium isopropylnaphthalene sulphonate, sodium methylenebisnaphthalene sulphonate, sodium ligninsulphonate or sodium dodecylbenzene sulphonate.

Moreover, the agricultural fungicidal compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the composition of the invention.

The above-mentioned carriers and various auxiliary agents may be used alone or in any desired combination, depending upon the type of preparation, the application and other factors.

In general, the fungicidal composition of the present invention may contain the compound of the invention in an amount of from 0.1 to 99% by weight, based upon the weight of the composition, although the precise amount of active ingredient in the composition will, naturally, depend upon the form of the composition, the manner in which it is to be applied and on whether or not the composition contains any other active ingredient.

For example, dusts may conveniently contain from 1 to 25% by weight of the compound of formula (I), the remainder being a solid carrier.

Wettable powders may conveniently contain, for example, from 25 to 90% by weight of the compound (I), the remainder being a solid carrier and a dispersing and wetting agent, if required, together with a protective colloidal agent, a thixotropic agent and an antifoaming agent.

Granules may conveniently contain from 1 to 35% by weight of the compound of formula (I), a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the compound of formula (I) and from 5 to 20% by weight of an emulsifying agent, the remainder being a liquid carrier, together with, if required, a corrosion inhibitor.

The fungicidal compositions of the present invention, which are formulated into the various types of preparation described above, may be applied to a paddy or upland (dry) field in an amount of from 1 to 5000 g, more preferably from 10 to 1000 g, of the compound of formula (I) per 10 ares for pre- or post-emergence fungicidal activity; they may be applied by foliage spraying, soil drenching, spraying onto irrigation water or any other known method.

The fungicidal composition of the present invention, when employed for seed disinfection or coating, may effectively control soil-borne or seed infectious diseases by coating seeds in an amount of from 0.1 to 2%, preferably from 0.2 to 0.5%, by weight of the compound of formula (I), based on the weight of the seed.

The fungicidal composition of the present invention may additionally contain other fungicides in order to broaden the fungicidal spectrum and, in some cases, a synergistic effect may be observed. The composition may also contain plant growth regulators, herbicides, insecticides or fertilizers, as is well known in the art.

The fungicidal compositions of the present invention may be used together with control agents effective against rice blast, helminthosporium leaf spot, bacterial leaf blight, rice stem borers, planthoppers and/or leafhoppers, to save the labour involved in separate applications. A combination of one or more of these additional control agents with the composition of the invention may be employed, depending upon the disease and/or the insect to be controlled and the form of the composition to be employed. We particularly prefer to employ the composition of the invention in the form of a dust, for the control of rice plant diseases and/or for soil treatment.

The efficacy of the compounds of the invention is illustrated by the following Experiments.

EXPERIMENT 1

Preventive effect against sheath blight on rice plants

Rice seedlings of the variety Nihonbare at the 4-5 leaf stage were sprayed with a test preparation containing 30 ppm of one of the active compounds listed in the following Table, in a total amount of 50 ml per 3 pots. The host plants were left at room temperature for 24 hours, and then 4-5 oat grains, on which the pathogenic fungus of sheath blight (*Rhizoctonia solani*) had previously been cultured, were placed around the lower part of the stem of each rice plant. The plants were then placed in a greenhouse maintained at 25°-27° C. and, 7 days after introduction of the fungus, were examined to determine the degree of damage, by measuring the height of each diseased spot in centimeters. The results are shown in the following Table, in which the heights of the spots are reported as averages over each group of 3 pots.

As a control, the same experiment was repeated, except that the seedlings were not treated with any fungicidal compound. These results are also shown in the Table.

EXPERIMENT 2

Preventive effect against sheath blight on rice plants by water surface application Rice seedlings of the variety Nihonbare at the 4-5 leaf stage were placed in pots and each pot was submerged in water to a depth of 1 cm. Test preparations containing one of the active compounds listed in the following Table diluted with water, were poured onto the irrigation water at the rate of 800 g of active ingredient per 10 ares. The pots were allowed to stand for 7 days in a greenhouse, after which the water was removed. 4-5 oat grains, on which the pathogenic fungus of rice sheath blight had previously been cultured, were placed around the lower part of the stem of each seedling. The plants were then placed in a greenhouse maintained at 25°-27° C. and, 7 days after introduction of the fungus, the host plants were examined to determine the degree of damage by measuring the height of each diseased spot in centimeters. Again, as a control, the experiment was repeated but without using any fungicidal compound. The results are also shown in the following Table.

EXPERIMENT 3

Preventive effect against damping-off on kidney beans, when employed as a seed dressing The pathogenic fungus *Rhizoctonia solani*, which had been cultured on an oat grain medium at 26° C. for 2 weeks, was thoroughly blended with soil. 60 grains of kidney beans, which had been dressed with a powder formulation containing one of the active ingredients shown in the following Table at a rate of 0.25% (as active ingredient, based on the weight of the grains), were sown in the soil, after which they were maintained in a greenhouse kept at 25° C. for 2 weeks. At the end of this time, the number of seedlings infected with the disease was determined. The same experiment was repeated, but without employing any fungicidal compound. The results are shown in the following Table.

TABLE

| Compound No. | Experiment No. 1 height of diseased spot (cm) | Experiment No. 2 height of diseased spot (cm) | Experiment No. 3 no. of diseased seedlings |
|---|---|---|---|
| 1 | 2.3 | 1.3 | 8 |
| 2 | 2.5 | 3.4 | 15 |
| 3 | 3.8 | 7.2 | 20 |
| 4 | 2.2 | 0 | 4 |
| 5 | 4.3 | 2.7 | 17 |
| 6 | 1.8 | — | — |
| 9 | 7.5 | — | — |
| 10 | 2.4 | 6.4 | 18 |
| 11 | 2.4 | 6.6 | 20 |
| 12 | 3.5 | — | — |
| 13 | 2.1 | 2.0 | 11 |
| 14 | 4.9 | — | — |
| 22 | 3.8 | — | — |
| 23 | 1.2 | — | — |
| 24 | 8.0 | — | — |
| 25 | 5.3 | — | — |
| 26 | 0.9 | — | — |
| 27 | 0.5 | — | — |
| 28 | 0.7 | — | — |
| 31 | 2.8 | — | — |
| 34 | 0.7 | — | — |
| Control | 18.4 | 17.6 | 60 |

We claim:

1. A process for preparing a compound of formula (I)

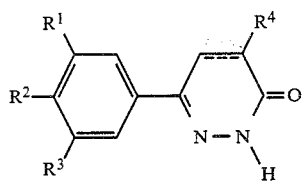  (I)

wherein:

$R^1$ and $R^3$ are the same or different and each represents a hydrogen atom or a halogen atom;

$R^2$ represents a hydrogen atom, a lower alkyl group, a lower alkoxy group or a halogen atom, provided that at least one of $R^1$, $R^2$ and $R^3$ represents a group or atom other than hydrogen;

⋯⋯⋯ represents a single or double carbon-carbon bond; and when ⋯⋯⋯ represents a single bond, $R^4$ represents a group of formula —$SR^5$ wherein $R^5$ represents (a) an alkyl group, (b) an alkyl group substituted with at least one selected from the group consisting of hydroxy, lower alkoxy, carboxy and alkoxycarbonyl, (c) a lower alkenyl group, (d) a phenyl group, (e) a substituted phenyl group (f) benzyl, (g) substituted benzyl, (h) phenethyl, (i) substituted phenethyl, (j) a pyridyl group or (k) a substituted pyridyl group said substituted phenyl, benzyl, phenethyl and pyridyl having at least one substituent selected from the group consisting of halogen, lower alkyl and nitro; and, when ⋯⋯⋯ represents a double bond, $R^4$ represents a hydrogen atom; which process comprises the steps (a) reacting a compound of formula (II)

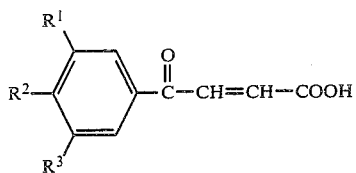  (II)

with a compound of formula (III)

$R^6H$  (III)

wherein $R^6$ represents (i) a group of formula —$SR^5$; (ii) a group of formula —$SR^7$ wherein $R^7$ represents a group of formula

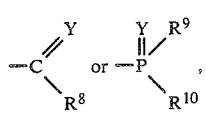

Y represents an oxygen atom or a sulphur atom, $R^8$ and $R^9$ each represent lower alkoxy groups and $R^{10}$ represents a lower alkoxy group, a lower alkyl group or a phenyl group; (iii) a methoxy group; or (iv) a halogen atom, provided that when $R^6$ represents a methoxy group, the reaction is effected in the presence of a hydrogen halide, to give a compound of formula (IV)

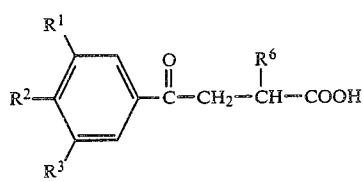  (IV)

and when $R^6$ represents the methoxy group, the methyl ester thereof;

(b) reacting the product of step (a) with hydrazine, (i) to give a compound of formula (V) when $R^6$ is —$SR^5$

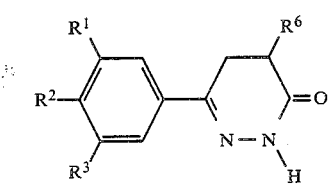  (V)

or (ii) a compound of formula (VI)

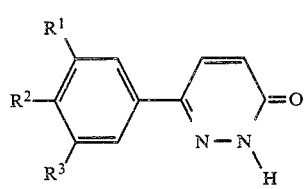  (VI)

provided that when the reaction of step (b) produces the compound of the formula (VI), when $R^6$ is —$SR^5$, the reaction with hydrazine is effected in the presence of an acid or a base, and when $R^6$ is methoxy or a halogen atom, the reaction with hydrazine is effected in the presence of an acid or followed by reaction with an acid.

2. A process as claimed in claim 1, which comprises the steps:

(a1) reacting said compound of formula (II) with a compound of formula $R^5SH$ (wherein $R^5$ is as defined in claim 1), to give a compound of formula (VIII):

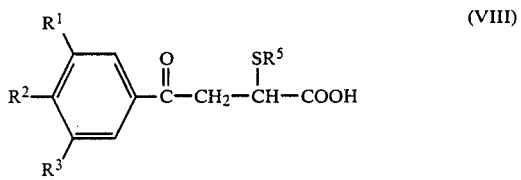

(wherein $R^1$, $R^2$, $R^3$ and $R^5$ are as defined in claim 1); and (b1) reacting said compound of formula (VIII) with hydrazine, to give a compound of formula (VII):

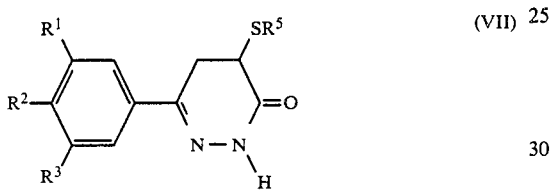

(wherein $R^1$, $R^2$, $R^3$ and $R^5$ are as defined in claim 1).

3. A process as claimed in claim 2, additionally comprising the step:

(c1) treating said compound of formula (VII) with an acid or a base to produce a compound of formula (VI):

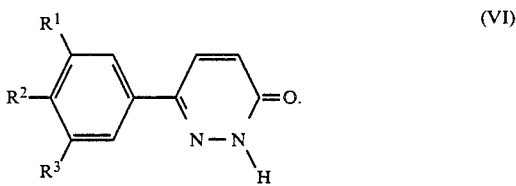

4. A process as claimed in claim 2 or claim 3, wherein $R^1$ represents a halogen atom and $R^2$ and $R^3$ both represent hydrogen atoms.

5. A process as claimed in claim 2 or claim 3, wherein $R^1$ and $R^3$ both represent halogen atoms and $R^2$ represents a lower alkyl group or a lower alkoxy group.

6. A process as claimed in claim 2, wherein $R^5$ represents an alkyl group, a 2-hydroxyethyl group, a carboxymethyl group, a carboxyethyl group, a (lower alkoxy)carbonylmethyl group or a (lower alkoxy)carbonylethyl group.

7. A process as claimed in claim 2 or claim 3, wherein $R^1$ and $R^3$ both represent chlorine atoms and $R^3$ represents a methyl group.

8. A process as claimed in claim 7, wherein $R^5$ represents a methyl, carboxymethyl, carboxyethyl, (lower alkoxy)carbonylmethyl or (lower alkoxy)carbonylethyl group.

9. A process as claimed in claim 2 or claim 3, wherein $R^1$ represents a bromine atom and $R^2$ and $R^3$ both represent hydrogen atoms.

10. A process as claimed in claim 9, wherein $R^5$ represents a methyl or 2-hydroxyethyl group.

11. A process as claimed in claim 3, wherein $R^1$ and $R^3$ both represent chlorine atoms, $R^2$ represents a methyl group and $R^5$ represents a lower alkyl group, an optionally substituted phenyl group or an optionally substituted aralkyl group, and wherein step (c1) is effected with an acid.

12. A process as claimed in claim 1, which comprises the steps:

(a2) reacting said compound of formula (II) with a compound of formula $R^7SH$ (wherein $R^7$ is as defined in claim 1) to give a compound of formula (IX):

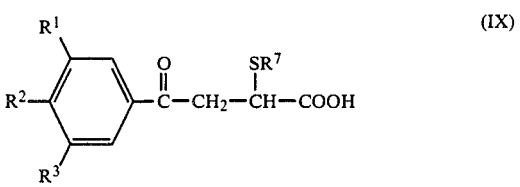

and (b2) reacting said compound of formula (IX) with hydrazine to produce said compound of formula (VI).

13. A process as claimed in claim 12, wherein said compound of formula $R^7SH$ is a monothiocarbonic acid or dithiocarbonic acid monoester and is employed in the form of an alkali metal salt.

14. A process as claimed in claim 13, wherein said salt is potassium O-ethyl dithiocarbonate or potassium O-ethyl thiocarbonate.

15. A process as claimed in claim 12, wherein said compound of formula $R^7SH$ is O,O-diethylthiophosphoric acid, O,O-dimethyldithiophosphoric acid, O,O-diethyldithiophosphoric acid, O,O-diisopropyldithiophosphoric acid, O,P-dimethyldithiophosphonic acid or O-ethyl-P-phenyldithiophosphonic acid.

16. A process as claimed in claim 12, wherein $R^1$ represents a halogen atom and $R^2$ and $R^3$ both represent hydrogen atoms.

17. A process as claimed in claim 12, wherein $R^1$ and $R^3$ both represent halogen atoms and $R^2$ represents a lower alkyl or lower alkoxy group.

18. A process as claimed in any one of claims 12 to 15, wherein $R^1$ and $R^3$ both represent chlorine atoms and $R^3$ represents a methyl group.

19. A process as claimed in any one of claims 12 to 15, wherein $R^1$ represents a bromine atom and $R^2$ and $R^3$ both represent hydrogen atoms.

20. A process as claimed in claim 1, which comprises the steps:

(a3) reacting said compound of formula (II) with methanol in the presence of a hydrogen halide to give a compound of formula (X):

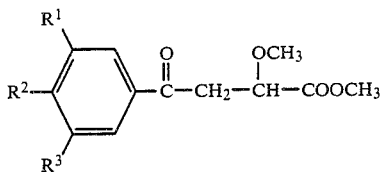

(wherein $R^1$, $R^2$ and $R^3$ are as defined in claim 1); and (b3) reacting said compound of formula (X) with hydrazine followed by or in the presence of an acid, to give said compound of formula (VI).

21. A process as claimed in claim 20, wherein said hydrogen halide is hydrogen chloride.

22. A process as claimed in claim 20, wherein $R^1$ represents a halogen atom and $R^2$ and $R^3$ both represent hydrogen atoms.

23. A process as claimed in claim 20, wherein $R^1$ and $R^3$ both represent halogen atoms and $R^2$ represents a lower alkyl group or a lower alkoxy group.

24. A process as claimed in claim 20 or claim 21, wherein $R^1$ and $R^3$ both represent chlorine atoms and $R^2$ represents a methyl group.

25. A process as claimed in claim 20 or claim 21, wherein $R^1$ represents a bromine atom and $R^2$ and $R^3$ both represent hydrogen atoms.

26. A process as claimed in claim 1, which comprises the steps:

(a4) reacting said compound of formula (II) with a hydrogen halide to give a compound of formula (XI):

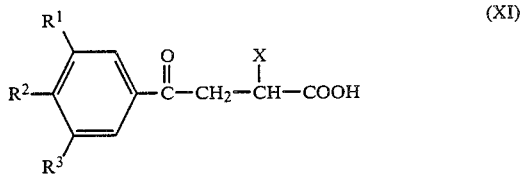

(wherein $R^1$, $R^2$ and $R^3$ are as defined in claim 1 and X represents a halogen atom); and (b4) reacting said compound of formula (XI) with hydrazine in the presence of or followed by an acid to give said compound of formula (VI).

27. A process as claimed in claim 26, wherein said hydrogen halide is hydrogen chloride and X represents a chlorine atom.

28. A process as claimed in claim 26, wherein $R^1$ represents a halogen atom and $R^2$ and $R^3$ both represent hydrogen atoms.

29. A process as claimed in claim 26, wherein $R^1$ and $R^3$ both represent halogen atoms and $R^2$ represents a lower alkyl goup or a lower alkoxy group.

30. A process as claimed in claim 26 or claim 27, wherein $R^1$ and $R^3$ both represent chlorine atoms and $R^2$ represents a methyl group.

31. A process as claimed in claim 26 or claim 27, wherein $R^1$ represents a bromine atom and $R^2$ and $R^3$ both represent hydrogen atoms.

32. A process for preparing 6-(3,5-dichloro-4-methylphenyl)-3(2H)pyridazinone, which comprises the steps:

(a5) reacting 4-(3,5-dichloro-4-methylphenyl)-4-oxo-2-butenoic acid with a thiol of formula $R^{12}SH$ wherein $R^{12}$ represents a lower alkyl group a phenyl group, a substituted phenyl group, an aralkyl group, or a substituted aralkyl group, said aralkyl group being benzyl or phenethyl and the substituents on said substituted phenyl and substituted aralkyl group are selected from the group consisting of halogen, lower alkyl and nitro to prepare a 2-(alkyl, phenyl)thio-4-(3,5-dichloro-4-methylphenyl)-4-oxobutyric acid, 2-(alkyl, substituted phenyl)thio-4-(3,5-dichloro-4-methylphenyl)-4-oxobutyric acid, 2-(alkyl, aralkyl)thio-4-(3,5-dichloro-4-methylphenyl)-4-oxobutyric acid, or a 2-alkyl, substituted aralkyl)thio-4-(3,5-dichloro-4-methylpheyl)-4-oxobutyric acid;

(b5) reacting the product of step (a5) with hydrazine to prepare a 4-(lower alkyl, phenyl)thio-6-(3,5-dichloro-4-methylphenyl)-4,5-dihydro-3(2H) pyridazinone, 4-(lower alkyl, substituted phenyl)thio-6-(3,5-dichloro-4-methylphenyl)-4,5-dihydro-3(2H) pyridazinone, 4-(lower alkyl, aralkyl)thio-6-(3,5-dichloro-4-methylphenyl)-4,5-dihydro-3(2H) pyridazinone, or a 4-(lower alkyl, substituted aralkyl)thio-6-(3,5-dichloro-4-methylphenyl)-4,5-dihydro-3(2H) pyridazinone; and (c5) reacting the product of step (b5) with an acid.

33. A process for preparing 6-(3,5-dichloro-4-methylphenyl)-3(2H)pyridazinone, which comprises reacting 4-(3,5-dichloro-4-methylphenyl)-4-oxo-2-butenoic acid with methanol in the presence of a hydrogen halide to prepare methyl 4-(3,5-dichloro-4-methylphenyl)-4-methoxy-4-oxobutyrate and reacting said methyl 4-(3,5-dichloro-4-methylphenyl)-4-methoxy-4-oxobutyrate with hydrazine in the presence of an acid.

34. A process for preparing 6-(3,5-dichloro-4-methylphenyl)-3(2H)pyridazinone, which comprises reacting 4-(3,5-dichloro-4-methylphenyl)-4-oxo-2-butenoic acid with a hydrogen halide to prepare a 4-(3,5-dichloro-4-methylphenyl)-2-halo-4-oxobutyric acid and reacting said 4-(3,5-dichloro-4-methylphenyl)-2-halo-4-oxobutyric acid with hydrazine in the presence of an acid.

35. A process as claimed in claim 33 or claim 34, wherein said hydrogen halide is hydrogen chloride.

* * * * *